US008790094B2

(12) United States Patent
Felber et al.

(10) Patent No.: US 8,790,094 B2
(45) Date of Patent: Jul. 29, 2014

(54) DIAPHRAGM VACUUM PUMP

(75) Inventors: Armin Felber, Lucerne (CH); Beda Weber, Sins (CH); Roland Koch, Bremgarten (CH); Etienne Furrer, Zug (CH)

(73) Assignee: Medela Holding AG, Baar (CN)

( * ) Notice: Subject to any disclaimer, the term of this patent is extended or adjusted under 35 U.S.C. 154(b) by 325 days.

(21) Appl. No.: 13/233,116

(22) Filed: Sep. 15, 2011

(65) Prior Publication Data

US 2012/0070323 A1  Mar. 22, 2012

(30) Foreign Application Priority Data

Sep. 17, 2010 (CH) .................................. 01502/10
Sep. 17, 2010 (CH) ................. PCT/CH2010/000225
Jul. 21, 2011 (CH) ................. PCT/CH2011/000171

(51) Int. Cl.
- *F04B 43/06* (2006.01)
- *F04B 43/04* (2006.01)
- *F04B 45/047* (2006.01)

(52) U.S. Cl.
CPC ............... *F04B 43/04* (2013.01); *F04B 45/047* (2013.01)
USPC .............. 417/395; 417/384; 417/394; 60/292

(58) Field of Classification Search
CPC .... F04B 43/0054; F04B 43/06; F04B 43/067; F04B 43/0736; A61M 1/1037; A61M 5/02141
USPC .............................. 417/384, 394, 395; 60/292
See application file for complete search history.

(56) References Cited

U.S. PATENT DOCUMENTS

| | | | |
|---|---|---|---|
| 5,262,068 A * | 11/1993 | Bowers et al. | ................. 210/767 |
| 5,644,177 A | 7/1997 | Guckel et al. | |
| 6,758,657 B1 | 7/2004 | McNaull et al. | |
| 7,094,217 B2 | 8/2006 | Fialkoff | |
| 8,070,455 B2 * | 12/2011 | Tinker | ............................. 417/16 |
| 2004/0087898 A1 | 5/2004 | Weniger | |

(Continued)

FOREIGN PATENT DOCUMENTS

| | | |
|---|---|---|
| DE | 1579774 | 8/1970 |
| EP | 1850005 | 10/2007 |

(Continued)

OTHER PUBLICATIONS

International Search Report for International Patent App. No. PCT/CH2011/000171, dated Oct. 20 2011.

(Continued)

*Primary Examiner* — Charles Freay
*Assistant Examiner* — Patrick Hamo
(74) *Attorney, Agent, or Firm* — McDonnell Boehnen Hulbert & Berghoff LLP

(57) ABSTRACT

A diaphragm vacuum pump has an electrically operated drive unit and a vacuum diaphragm, which separates a pump chamber into a drive-side part and a drive-remote part and which can be deflected by means of a movable part of the drive unit. The drive unit is an electromagnetic drive unit and the vacuum diaphragm is deflected in the direction of a linear movement generated electromagnetically in the drive unit. Preferably, a ventilation valve is also actuated the movable part. The vacuum pump is relatively small and compact and operates quietly. The vacuum pump is suitable in particular for "hands-free" applications of breastpumps.

10 Claims, 14 Drawing Sheets

(56) References Cited

U.S. PATENT DOCUMENTS

| | | |
|---|---|---|
| 2005/0065471 A1 | 3/2005 | Kuntz |
| 2005/0222536 A1 | 10/2005 | Silver |
| 2007/0078383 A1 | 4/2007 | Tashiro et al. |
| 2008/0039781 A1 | 2/2008 | Bjorge |
| 2008/0287037 A1 | 11/2008 | Solberg |
| 2009/0099511 A1 | 4/2009 | Sutrina et al. |

FOREIGN PATENT DOCUMENTS

| | | |
|---|---|---|
| GB | 2465797 | 6/2010 |
| WO | 96/22116 | 7/1996 |
| WO | 99/44650 | 9/1999 |
| WO | 02/102437 | 12/2002 |
| WO | 2008/057218 | 5/2008 |
| WO | 2008/137678 | 11/2008 |

OTHER PUBLICATIONS

International Search Report for Swiss Patent Application No. CH 1502/2010, dated Dec. 13, 2010.

International Search Report and Written Opinion for International Patent Application No. PCT/CH2010/000225, dated Jan. 5, 2011.

* cited by examiner

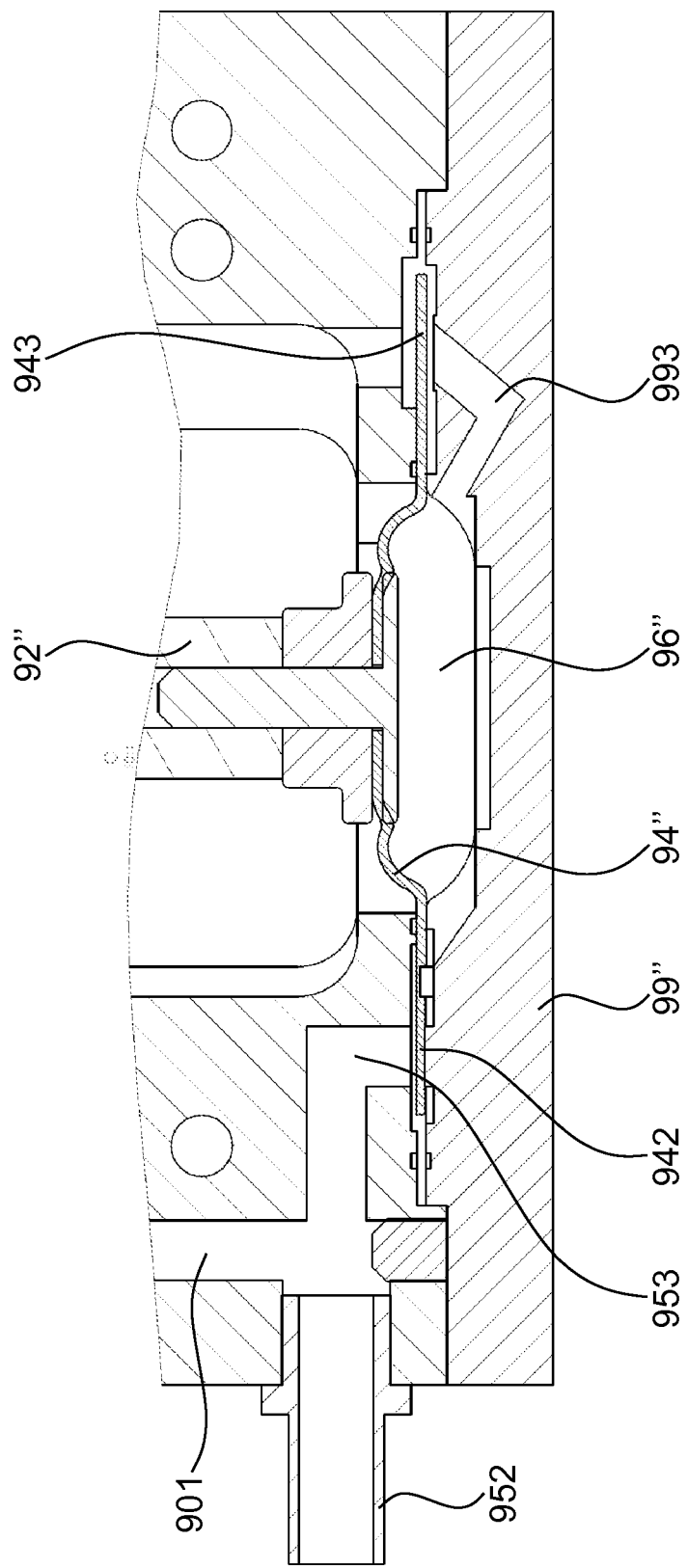

DIAPHRAGM VACUUM PUMP

CROSS REFERENCE TO RELATED APPLICATIONS

The present application claims priority to Swiss Patent Application No. 01502/10 filed on Sep. 17, 2010 the contents of which are fully incorporated by reference therein. The present application also claims priority to PCT Patent Application No. PCT/CH2010/000225 filed on Sep. 17, 2010, and PCT Patent Application No. PCT/CH2011/0001711 filed on Jul. 21, 2011, the contents of which are fully incorporated herein by reference.

TECHNICAL FIELD

The present invention relates to a diaphragm vacuum pump.

BACKGROUND

Diaphragm vacuum pumps may be used for various medicinal applications, in particular for drainage applications, such as wound drainage or thorax drainage. Diaphragm pumps are also well known as breastpumps for expressing human breast milk. Examples thereof include WO 96/22116, US 2009/0099511, US 2008/0287037, U.S. Pat. No. 7,094,217 and US 2008/0039781.

A drive of the vacuum pump customarily includes an electric motor which transmits rotational movement of a motor to a diaphragm via an eccentric, a connecting rod or another force transmission unit and cyclically deflects the diaphragm. A disadvantage of many pumps is that they are relatively large and loud. However, in particular in "hand-free" applications, the pump should be designed to be discrete, small, and quiet. In this context, "hands-free" means that, after being switched on, the entire device functions without hands, i.e. neither the pump nor the breast shield are held by hand.

WO 02/102437 and WO 2008/137678 show examples of "hands-free" expressing devices. The breast shield discussed is integrated in a pump housing and serves at the same time as a diaphragm for generating a negative pressure. A stepper motor may be used as the drive.

SUMMARY

It is an object of the invention to provide a vacuum pump which is designed to be small.

The diaphragm vacuum pump according to the invention has an electrically operated drive unit and a diaphragm which separates a pump chamber into a drive-side part and a drive-remote part, and which can be deflected by the drive unit. According to the invention, the drive unit is an electromagnetic drive unit and the membrane is deflected in the direction of a linear movement that is generated electromagnetically in the drive unit.

Drive units of this type can be of small design. Since the unit is directly coupled to the diaphragm, and because of the deflection of the diaphragm in the same direction as the electrically movable part of the unit, complicated and space-consuming force transmission elements are not necessary.

It is furthermore advantageous that, in comparison to the otherwise customary rotating drives of diaphragm vacuum pumps, the linear movement is quieter, and fewer vibrations and structure-borne sound are generated. In addition, in contrast to known diaphragm vacuum pumps, the stroke length can be changed and can be controlled electronically. This permits precise control even under high vacuum levels.

In a preferred embodiment, the drive unit has at least one permanent magnet and a coil former with a coil, the coil being arranged on the coil former, and the coil former together with the coil is held in a linearly displaceable manner along a longitudinal axis with respect to the magnet. The coil former is connected to the diaphragm and deflects the latter during the abovementioned displacement of the coil former in the direction of the displacement of the coil former.

The coil former preferably has a length which is greater than its width. The coil former may be formed as a single piece or in a number of pieces. The diaphragm preferably has a diameter that is larger than the piston. The diaphragm is preferably of substantially circular design and is composed of a thin material, such as silicone, for example.

The coil former preferably serves as piston for the deflection of the diaphragm. The piston has a first end at which the diaphragm is arranged. Force is therefore transmitted directly and precisely. The deflection of the diaphragm can be controlled in a specific manner and the vacuum pump operates within a narrow tolerance limit. The precision can be further increased if the diaphragm is fastened centrally to the first end of the piston.

The vacuum pump typically operates up to a negative pressure of 0 to 300 mmHg. The diaphragm can be driven at a frequency of 5 to 120 cycles per minute.

The piston has a second end, which, in a first preferred embodiment, is held in a linearly displaceable manner.

As an alternative, a second diaphragm can also be fastened to the second end of the piston. The second diaphragm is preferably formed identically to the first diaphragm and is likewise arranged in a pump chamber. There is therefore a double pump, which is of mirror-symmetrical design preferably centrally with respect to the longitudinal axis thereof.

In a preferred embodiment, the movable part of the pump unit is operatively connected to a ventilation valve, and therefore the linear movement of the movable part of the unit is optionally also used at the same time in order to actuate the ventilation valve. In a preferred embodiment, the ventilation valve is arranged for this purpose at that end of the movable unit part which is opposite the vacuum diaphragm. Upon an appropriate stroke, the movable unit part opens the ventilation valve. The unit part preferably has at least one pin which acts on at least one valve flap such that the valve flap opens up a ventilation opening. The valve flap is preferably part of a ventilation diaphragm that is fastened to the movable unit part.

Since the movable unit part may also be used for actuating the ventilation valve, the construction of the unit is simplified, and relatively few individual parts are required. It is advantageous that a separate motor and a separate controller are not required in order to actuate the ventilation valve. This increases the reliability and reduces the cost of the pump unit.

It is furthermore advantageous that both diaphragms, i.e. the vacuum diaphragm and the ventilation diaphragm, serve as a mounting for the movable part of the unit, thus avoiding friction. The pump unit can therefore be used for a relatively long time without maintenance.

In a preferred exemplary embodiment, in particular in the above-mentioned examples, the coil is a flat coil and there are at least two permanent magnets which are arranged on either side of the coil and of the coil former. Preferably there is a pair of permanent magnets each on either side of the coil.

In another preferred exemplary embodiment, the second end of the piston is mounted displaceably between an iron core and a magnet.

The coil may be a moving coil, wherein the moving coil and the permanent magnet are of rotationally symmetrical design and the iron core passes through the moving coil.

There is preferably a position detector for determining the relative position of the coil former with respect to the permanent magnet. As a result, the particular deflection of the diaphragm can also be determined unambiguously. The position detector is preferably an optical sensor. For example, a position scale, which is monitored by the optical sensor, can be arranged on the coil former. The position scale can consist, for example, of one, two, or more grayscale bands which move together with the coil former relative to the sensor.

If the position detector generates a signal, which is used to control the pump, as a function of the relative position of the coil former, the deflection of the diaphragm can be controlled precisely. The vacuum pump operates within a narrow tolerance range with respect to frequency and amplitude, i.e. with respect to the vacuum obtained.

The vacuum pump is suitable for a very wide variety of areas of application, in particular for medicinal use. A further preferred application is the expressing of human breast milk, i.e. in the area of breastpumps. Other preferred applications are thorax drainage and wound drainage.

In a preferred breastpump, which has the pump unit according to the invention, there is an outlet in the drive-remote part of the pump chamber, the outlet being connected to an inlet of a second chamber, wherein the chamber has a second diaphragm which separates the chamber into two parts. This diaphragm serves as a means of separating media and for transferring the generated vacuum outward. The second diaphragm can give rise to a system which changes from an initial pneumatic negative pressure in a breast shield bearing against the breast to a hydraulic negative pressure. In this case, milk which is already being expressed acts as fluid of the hydraulic system which expresses further milk out of the breast.

However, the vacuum pump according to the invention can also be used for breastpumps which apply a cyclic vacuum to the breast shield and in which the milk passes into a milk collecting container via a path that is separate from the air line.

BRIEF DESCRIPTION OF THE FIGURES

Preferred embodiments of the invention are described below with reference to the drawings that serve merely for explanation and should not be interpreted as being limiting. In the drawings:

FIG. 17 shows an enlarged detail C according to FIG. 15.

The same parts are provided with the same reference numbers in the Figures.

DETAILED DESCRIPTION

Figure 1:
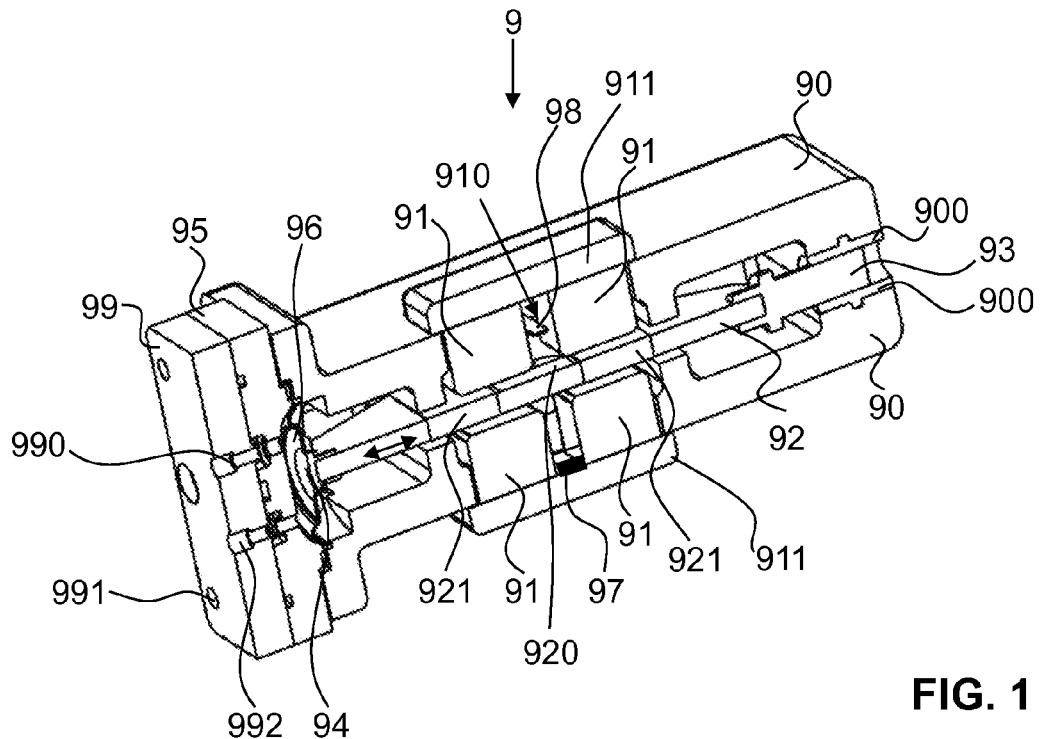
FIG. 1 shows a longitudinal section through a vacuum pump according to the invention.

FIG. 1 illustrates a first embodiment of the vacuum pump unit with an electromagnetic drive according to the invention.

The pump unit has a housing 90, which is preferably manufactured from metal or plastic. The housing 90 may have a cuboidal design. A flat iron core, which is here an iron plate 911, and a permanent magnet 91 attached to the iron plate 911 are arranged on one side of the housing 90. The iron plate 911 rests upon the housing 90 such that the permanent magnet 91 is in a recess of the housing. In this embodiment, the permanent magnet 91 includes, and preferably consists of, two parts, which are spaced from one another such that there is a recess 910 between both parts.

An identical construction may be present on an opposite side of the housing. An iron plate 911 and a two-part permanent magnet 91 attached to the iron plate 911 are also arranged on the opposite side of the housing.

A flat coil former 92 with a coil 921 inserted in the coil former 92 runs between the two mutually opposite pairs of permanent magnets 91.

The coil former 92 is of substantially rod-shaped or plate-shaped design. At one end, the coil former 92 is held in a fixed position in a guide bearing 93. The guide bearing 93 is displaceable together with the coil former 92 including the coil 921 relative to the housing 90 and therefore relative to the permanent magnet 91 along the longitudinal axis of the housing 90. For this purpose, the housing 90 has a plain bearing 900. The movement of the coil former 92 is illustrated by a double arrow in FIG. 1.

The other end of the coil former 92 is fixedly connected to a diaphragm, referred to here as the vacuum diaphragm 94. The vacuum diaphragm 94 bears against the housing 90 on an end side and is clamped securely between the housing 90 and a valve plate 95. The diaphragm 94 separates a pump chamber 96 from the coil former 92. The vacuum diaphragm 94 preferably has a circular outline, a shape customary for diaphragms of diaphragm vacuum pumps. The valve plate 95 is held between the housing 90 and a cover 99. The three parts are preferably connected, for example screwed, tightly to one another in a detachable or nondetachable manner. The corresponding holes are provided with the reference number 991 in the cover 99. The cover 99 has a port opening 990 for the vacuum line 12' which is connected to the pump chamber 96. An air inlet opening 992 in the cover 99 likewise connects the environment to the pump chamber 96 via the valve plate 95. The valve plate 95 has the valves, inlets and outlets customary for diaphragm vacuum pumps. These are not described in detail here.

If an alternating electric current flows through the coil 921, the electromagnetic field changes and the coil former 92 moves relative to the permanent magnet 91. The coil former 92 acts like a piston or ram and moves the vacuum diaphragm 94 cyclically back and forth. In this case, the force acting on the vacuum diaphragm 94 is proportional to a current applied to the coil. By means of the movement of the vacuum diaphragm 94, a cyclically changing vacuum is built up in the pump chamber 96 and is present at the output 990.

The vacuum diaphragm 94 of the pump unit 9 is driven via a linear movement that is generated electromagnetically, wherein the coil former 92 acts as a piston. It is advantageous that, in comparison to the rotating drives that are otherwise customary, the movement is quieter, and fewer vibrations and less structure-borne sounds are generated. In contrast to the prior art, the stroke length can be changed, and can be electronically controlled. This permits precise control even under low vacuum levels.

In order for the stroke length to be controlled in a specific manner, the displacement and/or the position of the coil former 92 is monitored, such as by position and/or movement sensors, for example. In this example, this takes place by means of an optical sensor which detects a position scale. The position scale 920 is preferably provided on the coil former 92. A light source 97 sends its light perpendicularly to the longitudinal direction of the coil former 92 to an opposite detector 98, the light passing through the position scale 920. The coil former 92 in the region is of a transparent design.

The position scale may be formed, for example, by one, two or more grayscale bars which, together with the coil former, pass the sensor. If there are two grayscale bars running parallel to each other, wherein one has a rising graduation and one has a falling graduation, and two sensors are used, the difference between the two signals can be used as a precise determination of the position.

The light source 97 and the detector 98 are preferably arranged in the recesses 910 of the permanent magnet 91. Other types of position measurements are possible. The measured signal is sent to an electronic controller of the vacuum pump and the current is applied to the coil according to the signal. As a result, the position, the deflection amplitude, and the frequency can be controlled independently of one another. Vacuum values of 0 to 300 mmHg are customarily obtained. The frequencies are customarily 0 to 150 cycles per minute.

As an alternative, instead of the guide bearing 93, there may also be a second diaphragm which is of similar or identical design to the vacuum diaphragm 94. This results in a symmetrical construction, which likewise ensures guidance and therefore a linear movement of the coil former 92 within the housing 90. In addition, the second diaphragm can be used to build up the vacuum such that the flow rate can be increased.

Figure 2:
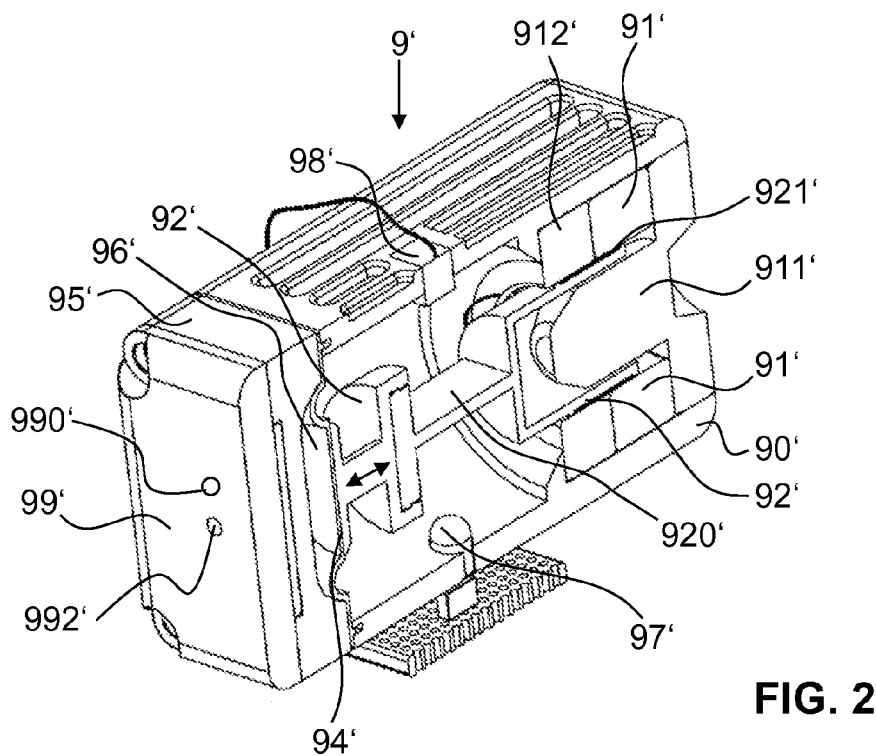
FIG. 2 shows a longitudinal section through a vacuum pump according to the invention in a second embodiment.

FIG. 2 shows a second embodiment of a vacuum pump with an electromagnetically generated linear driving movement of the diaphragm. In contrast to the above-described flat coil, a moving coil is used. The magnet and coil are of rotationally symmetrical, in particular annular and cylindrical design, respectively. A housing 90' is also present. A permanent magnet 91' is arranged at the rear end of the moving coil remote from the breast shield. The permanent magnet is passed through by an iron core 911', which is in contact with the permanent magnet 91' on a first end side thereof. Against the opposite end side of the permanent magnet bears an iron ring 912'. The coil former 92' engages around the iron core 911' and is axially guided by the iron core. The coil former 92' extends between the iron core 911' and the permanent magnet 91' and the iron ring 912', respectively. The coil former 92' is guided without contact in the permanent magnet 91' and in the iron ring 912'. The wound coil 921' surrounds the coil former 92' in this region.

The coil former 92' is also fixedly connected to the vacuum diaphragm 94' and acts as a piston for the linear drive of the vacuum diaphragm 94'. The pump chamber is provided with the reference number 96', the valve plate with the reference number 95' and the cover with the reference number 99'. The port opening has the reference number 990' and the air inlet opening has the reference number 992'. Also here, there is again a position sensor which indicates the position of the coil former 92' relative to the magnet 91' and therefore the movement and the position of the vacuum diaphragm 94', respectively, to a controller in order to control the vacuum. The light source is denoted here by the reference number 97', the detector by 98' and the position scale by 920'. The position scale is preferably in a transparent design. In contrast to the previous example, the sensor here is arranged outside the region of the permanent magnet 91'.

In this embodiment, vacuum values of 0 to 300 mmHg are customarily obtained. The frequencies are customarily 0 to 150 cycles per minutes.

FIGS. 7 to 17 show a third embodiment of a vacuum pump according to the invention with electromagnetically generated linear driving movement of the diaphragm. This embodiment essentially constitutes a development of the pump unit according to FIG. 1.

Figure 7:
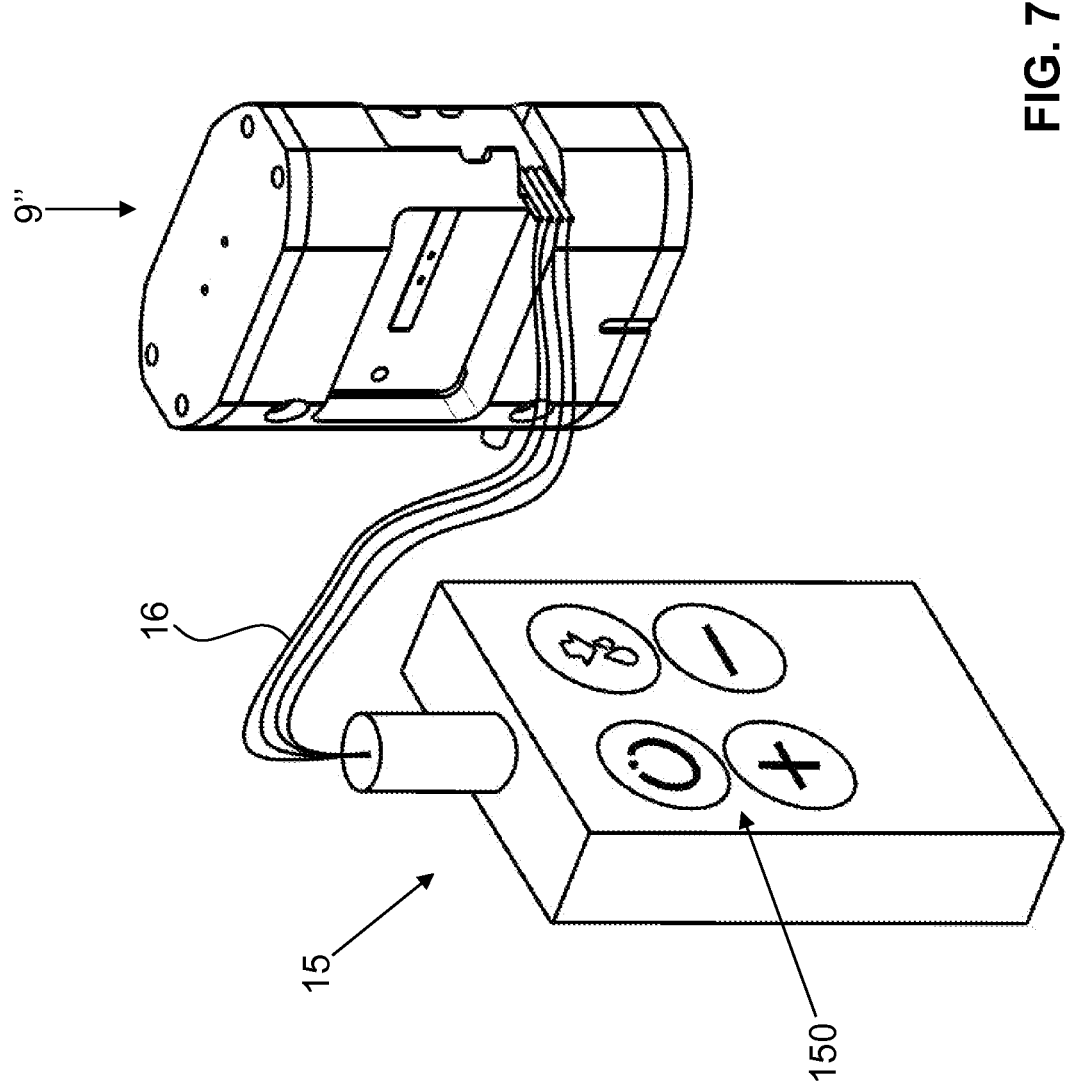
FIG. 7 shows a schematic view of a vacuum pump according to the invention in a third embodiment including the control unit.

FIG. 7 shows the pump unit 9" according to third embodiment, the pump unit being connected to a control unit 15 via lines 16 for supplying current and for the transfer of data. The control unit 15 has operating elements 150 for operating the breastpump.

Figure 8:
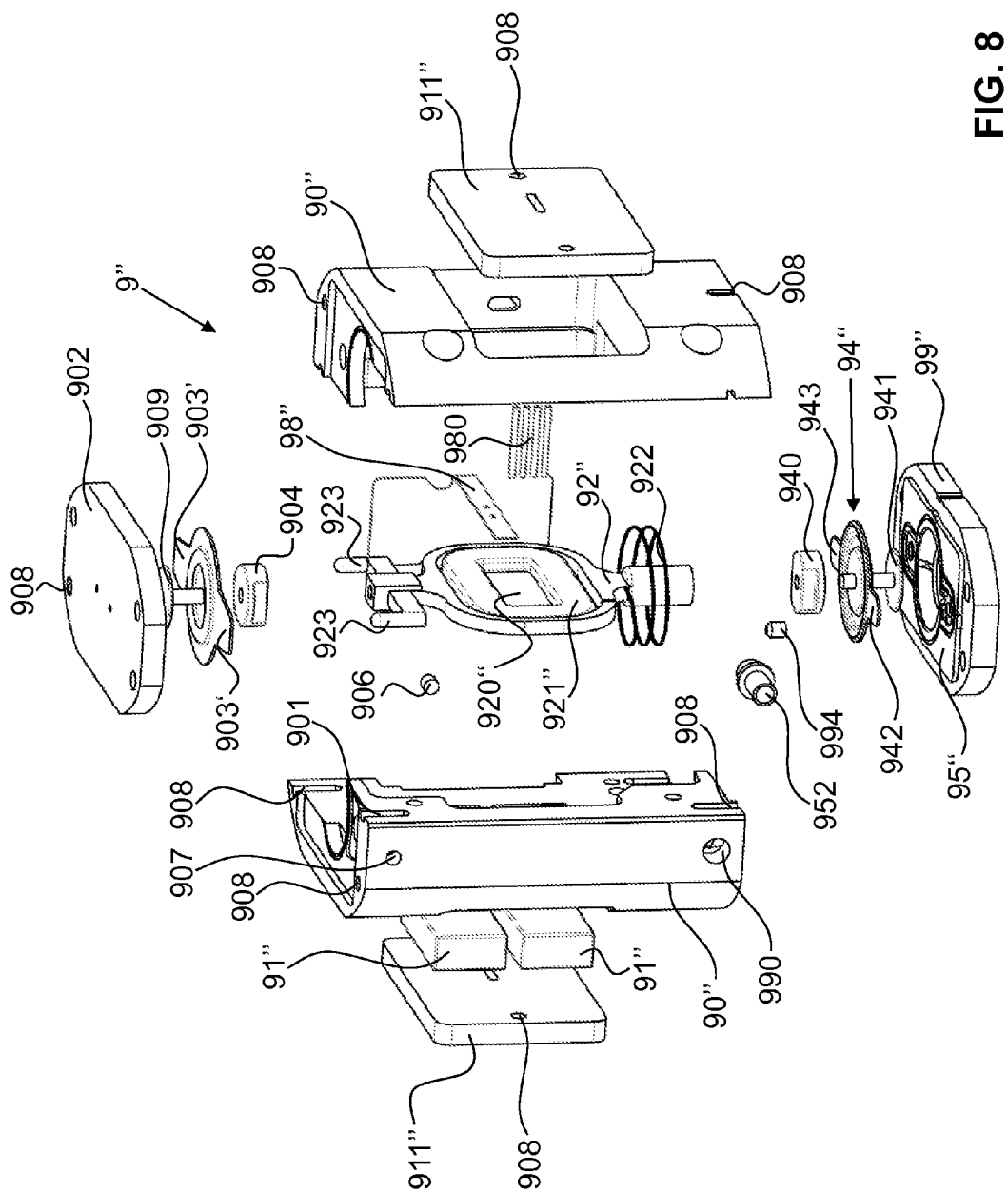
FIG. 8 shows an exploded view of the vacuum pump according to FIG. 7.
Figure 9:
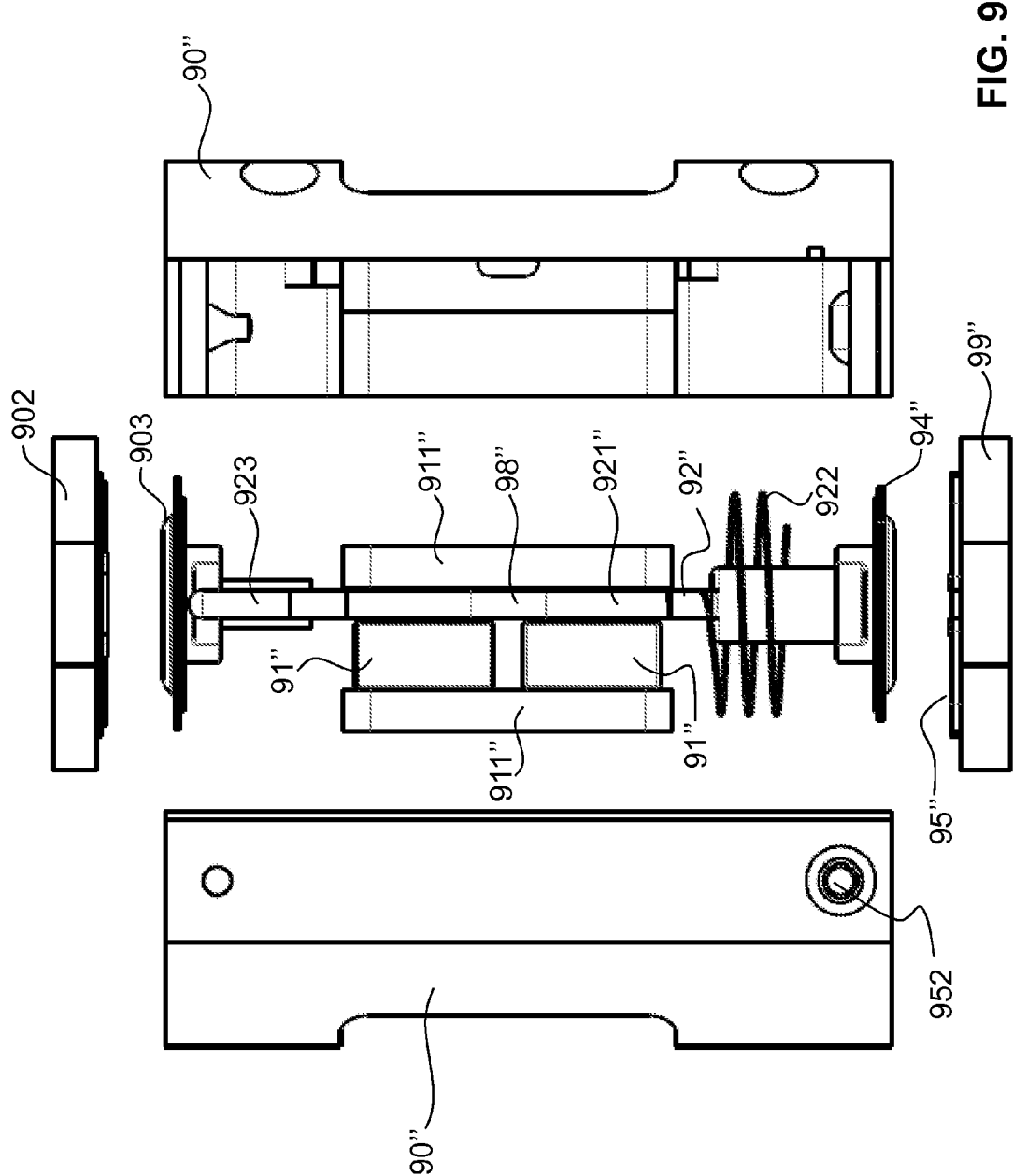
FIG. 9 shows a side view of the vacuum pump according to FIG. 7 in a partially assembled state.

FIG. 9 shows the pump unit 9" in a partially exploded view. The individual parts of the unit 9" can readily be seen in FIG. 8. The pump unit 9" has a housing 90" that is preferably manufactured from metal or plastic. The housing 90", formed by two side parts 90", is closed on both sides by a planar cover 99", 902. The corresponding fastening holes 908 in the housing 90" and in the covers 99", 902 can be seen in FIG. 8. The associated screws are not illustrated.

A coil carrier or coil former 92" with a flat coil 921" fastened thereto is arranged in the housing. End windings 922 of the coil 921" surround a rod-shaped end of the coil former 92". The rod-shaped end preferably has a round cross section.

The coil 921" has a central recess, in which a position scale 920" is arranged. The position of the coil former 92" relative to the housing can be ascertained by means of an opposite transmitter and receiver or detector 98" on the basis of the position scale 920". The transmitter/receiver 98" preferably comprises a light-emitting diode and a photodiode. The position scale 920" may be, for example, a grayscale scale. The ports for an associated measuring board are denoted in the figure by the reference numeral 980. Other means of determining the position are possible.

An iron plate 911" is arranged on one side of the coil former 92". There are permanent magnets 91" connected to a second iron plate 911", that is connected to the permanent magnets and connects the permanent magnets 91" to one another, on the other side. In this embodiment, the permanent magnets 91" are preferably of cuboidal design. They may also be arranged on both sides of the coil 921", as in FIG. 1. Similarly, the magnets 91 of the embodiment according to FIG. 1 may also be present only on one side of the coil.

Figure 12:
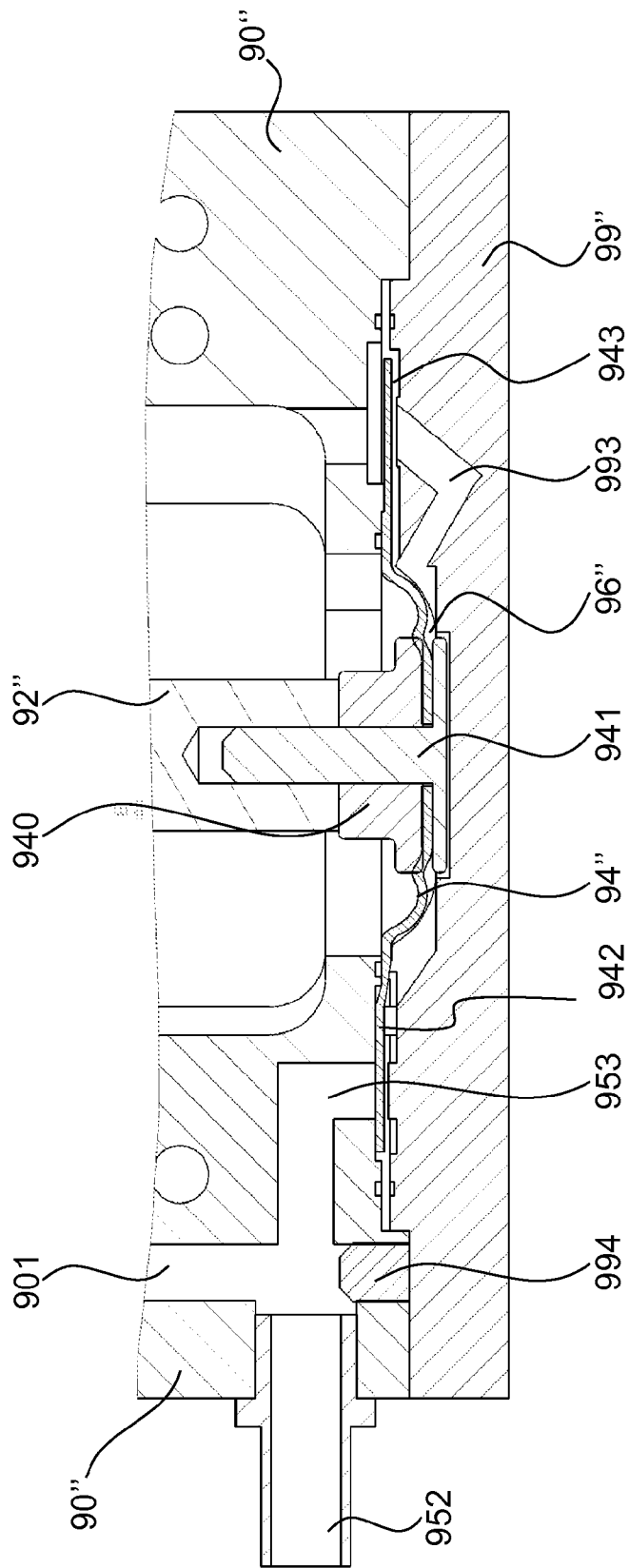
FIG. 12 shows an enlarged detail E according to FIG. 10 with an open exhaust flap and closed vacuum flap.

A vacuum diaphragm 94" is arranged on one side of the elongate coil former 92" and is fixedly connected to the coil former 92". The vacuum diaphragm 94" has a known, preferably round shape with grooves or beads and is preferably substantially plate-shaped. The vacuum diaphragm 94" is preferably manufactured from an elastic material, such as silicone, for example. For the fastening to the coil former 92", the diaphragm is provided with a central hole, as shown in FIG. 12.

The vacuum diaphragm 94" preferably has two wings which are diametrically opposite each other and are formed integrally with the rest of the diaphragm 94". The two wings form an inlet valve flap or vacuum flap 942 and an outlet valve flap 943.

The vacuum diaphragm 94" is fastened to the first end of the coil former 92" with clamping means. There is a first spacer 940 and a counterpart 941 for this purpose, as can be seen in FIGS. 8 and 12. For this purpose, the counterpart 941 has a plate and a stud which is integrally formed thereon. The first spacer 940 is of cuboidal design with a hole for receiving the stud. The counterpart 941 is arranged on the lower side of the diaphragm 94", the stud penetrates the diaphragm 94" and the first spacer 940 and engages in an opening in the lower end of the coil holder 92". The stud and the opening preferably each have a thread.

A valve plate 95" is arranged in the cover 99". The valve plate may be inserted into a corresponding recess of the cover 99" or may be formed integrally in the cover. The valve plate 95" has valve openings and valve channels that are customary for diaphragm pumps and are connected to the valve flaps 942, 943.

A vacuum port 952, which can readily be seen in FIGS. 8 and 12, leads outward such that a vacuum generated in the pump unit, or more precisely in a pump chamber 96', can be applied externally, for example in a breast shield of a breastpump. Pump chamber 96" and vacuum port 952 are connected to each other via a vacuum channel 953. There is a corresponding port opening 990 in the housing 90" in order to guide the vacuum port 952, here a nozzle, outward.

According to the invention, a second diaphragm 903 is arranged at that end of the coil former 92" which is opposite the vacuum diaphragm 94". The second diaphragm 903 together with the rear-side cover 902 forms a valve that serves to ventilate the unit, or more precisely the vacuum channel 953 and therefore the vacuum port 952. With the aid of the ventilation diaphragm 903, an externally applied vacuum can be reduced rapidly and in a specific manner such that the pressure in the vacuum channel 953 and at the vacuum port 952 is increased, depending on the duration of the ventilation, to atmospheric pressure. The air for the ventilation originates from the interior of the housing 90", the housing not being hermetically closed to the outside except in the regions relevant to the generation of the vacuum.

The ventilation diaphragm 903 is likewise fixedly connected to the coil former 92". The ventilation diaphragm 903 is preferably round with grooves or beads, i.e. is of plate-shaped design, and has two diametrically opposite wings, wherein at least one of the wings, preferably both wings, forms or form a ventilation flap 903'. The ventilation diaphragm 903 may be of substantially identical design to the vacuum diaphragm 94". However, it may also have a different shape and/or size.

The ventilation diaphragm 903 has a central hole so that it can be fastened to the rear-side cover 902 with suitable clamping means. The clamping means are preferably a second spacer 904 and a counterpart 909. The second spacer 904 and the counterpart 909 are preferably of identical design to the corresponding parts for the fastening of the vacuum diaphragm 94". A stud of the counterpart 909 is also received here in a corresponding opening in the second end of the coil former 92".

At least one, here two, ventilation actuators 923, protrude over the second end of the coil former 92". In this example, each ventilation actuator 923 is a pin which is directed towards the ventilation flaps 903' and runs in the axial direction of the coil former 92'. The pins 923 are arranged on the coil former 92' and are preferably formed integrally therewith. They are arranged diametrically opposite one another. The distance of the pins 923 from the center axis of the coil former 92' is dimensioned such that the pins can touch the ventilation flaps 903'. It is also possible to use only a single pin. However, for reasons of symmetry, in particular in order to permit a uniform movement of the coil former 92", the use of two or more pins is recommended.

Figure 10:
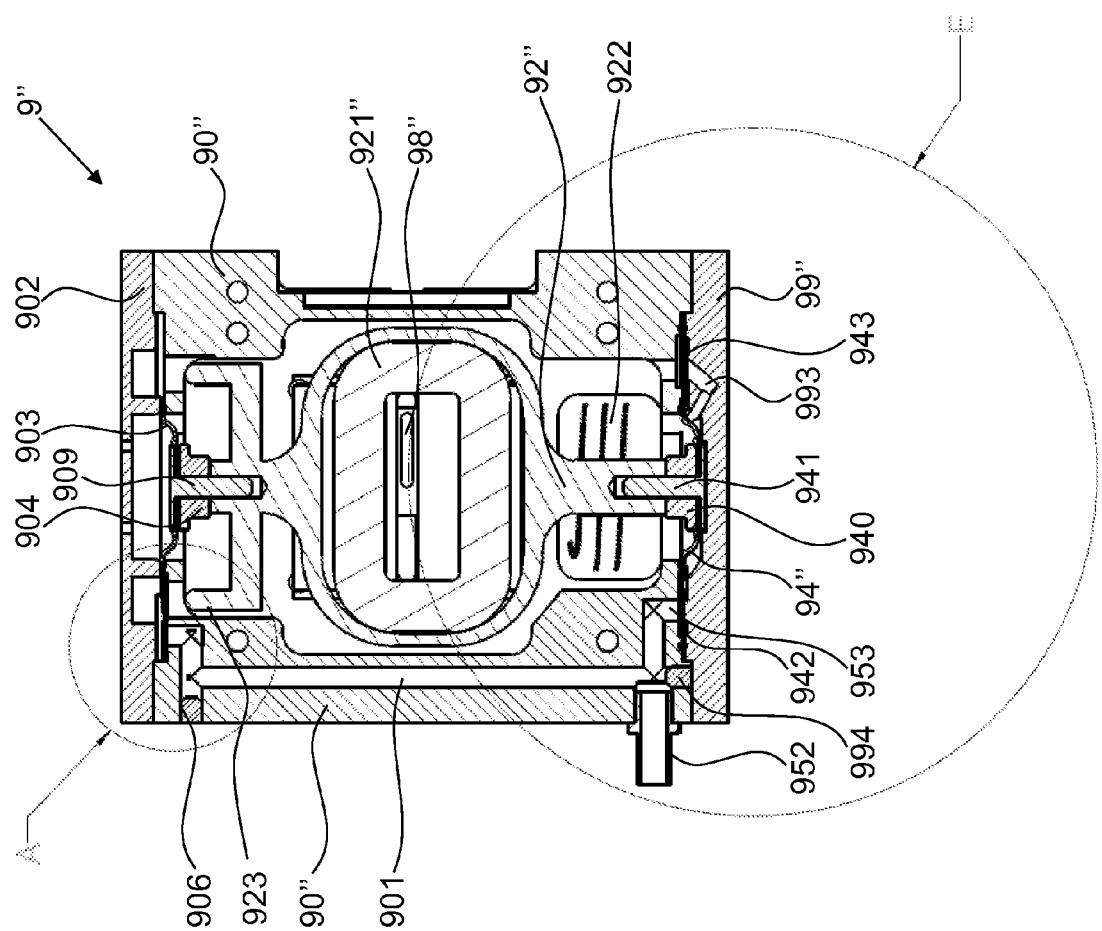
FIG. 10 shows a longitudinal section through the vacuum pump according to FIG. 7 in a first position during the generation of the vacuum.
Figure 11:
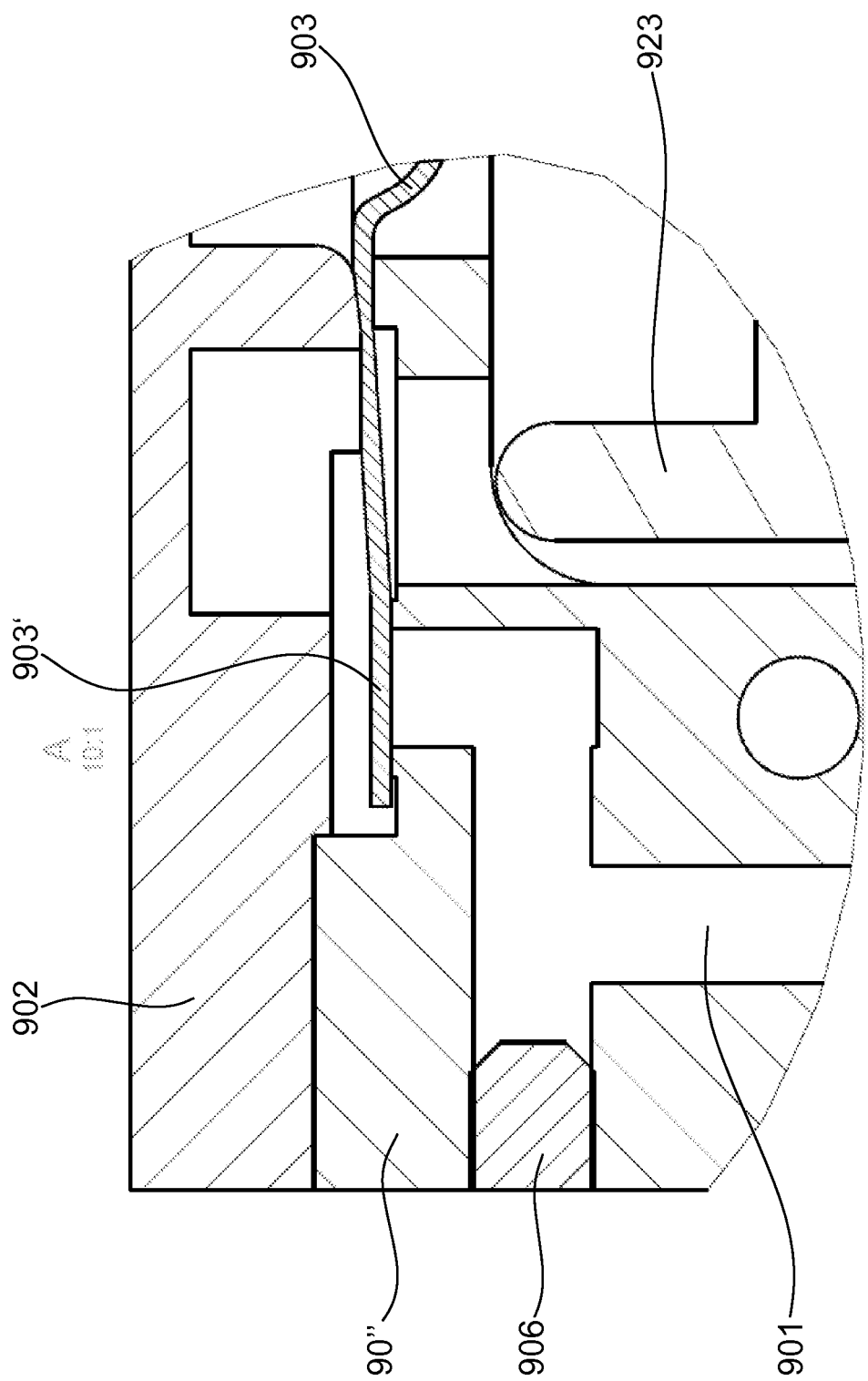
FIG. 11 shows an enlarged detail A according to FIG. 10 with a closed ventilation flap.

FIG. 10 shows a cross section through the assembled unit. The unit is in a first maximum stroke position, in which a vacuum is generated. The coil former 92" is in a position close to the vacuum chamber 96", called the lower position here. It can be seen in FIG. 11 that the ventilation diaphragm 903 rests on the housing 90" and the ventilation flaps 903' close a ventilation channel 901 running in the housing 90". For the purpose of simpler production, the ventilation channel 901 is provided at one end with a closure stopper 906 in order to close a corresponding bore 907 in the housing 90". For the same reason, the other end of the ventilation channel 901 is likewise provided with a closure stopper 994. The ventilation diaphragm 903 is preferably prestressed in order optimally to ensure the closure.

FIG. 12 shows the situation at the same point in time in the lower region containing the vacuum diaphragm 94". The vacuum diaphragm 94" is in the lowermost position thereof, in which it is at its closest to the cover 99". The vacuum valve flap 942 is closed, and the connection between pump chamber 96" and vacuum channel 953 is interrupted. By contrast, the outlet valve flap 943 is open. As a result, air still in the cover-side region of the pump chamber 96" is released into the housing 90" or to the outside via an outlet channel 993 running in the valve plate 95' and in the cover 99", respectively.

Figure 13:
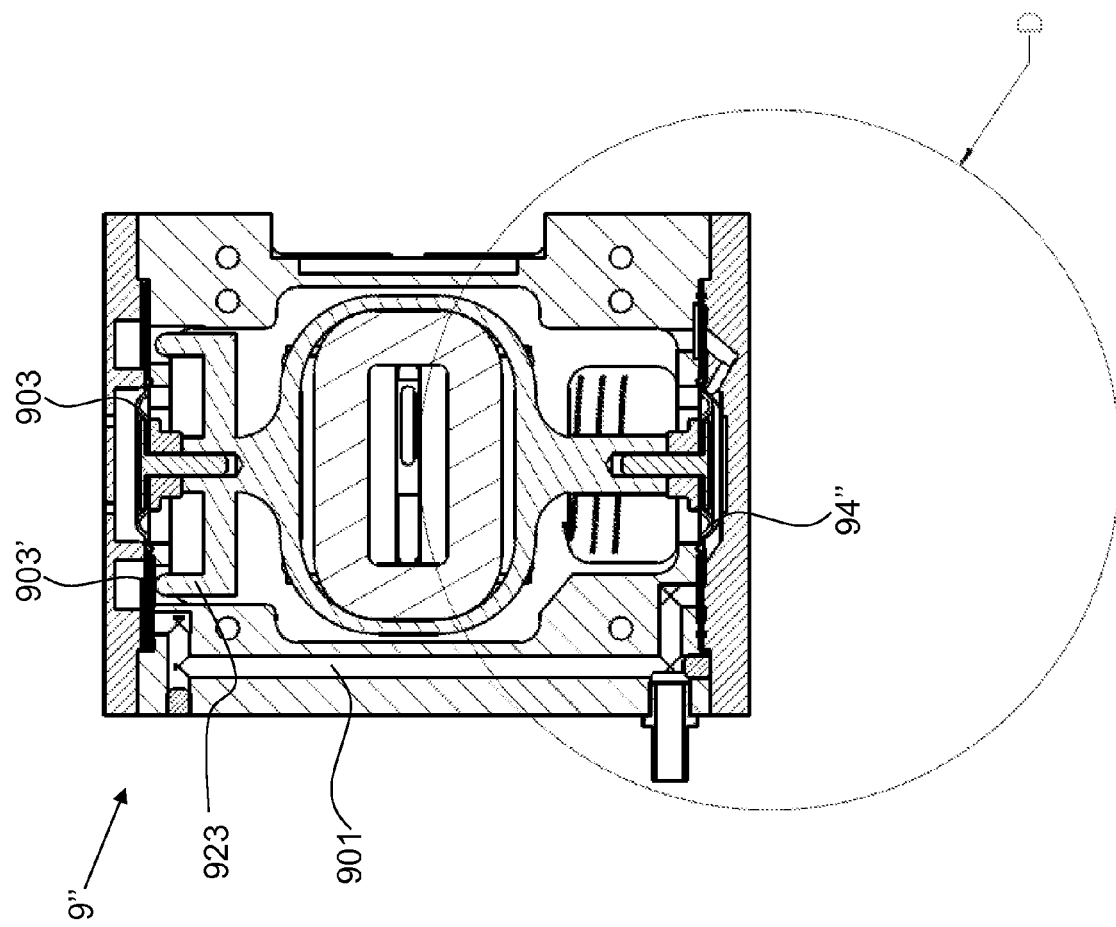
FIG. 13 shows a longitudinal section through the vacuum pump according to FIG. 7 in a second position during the generation of a vacuum.

FIG. 13 shows the coil former 92" in a second stroke position. As before, the ventilation diaphragm 903 closes the ventilation channel 901 such that air cannot pass from the outside into the vacuum channel 953. Although the ventilation actuator 923 has come closer to the ventilation flap 903', it is not yet raised.

Figure 14:
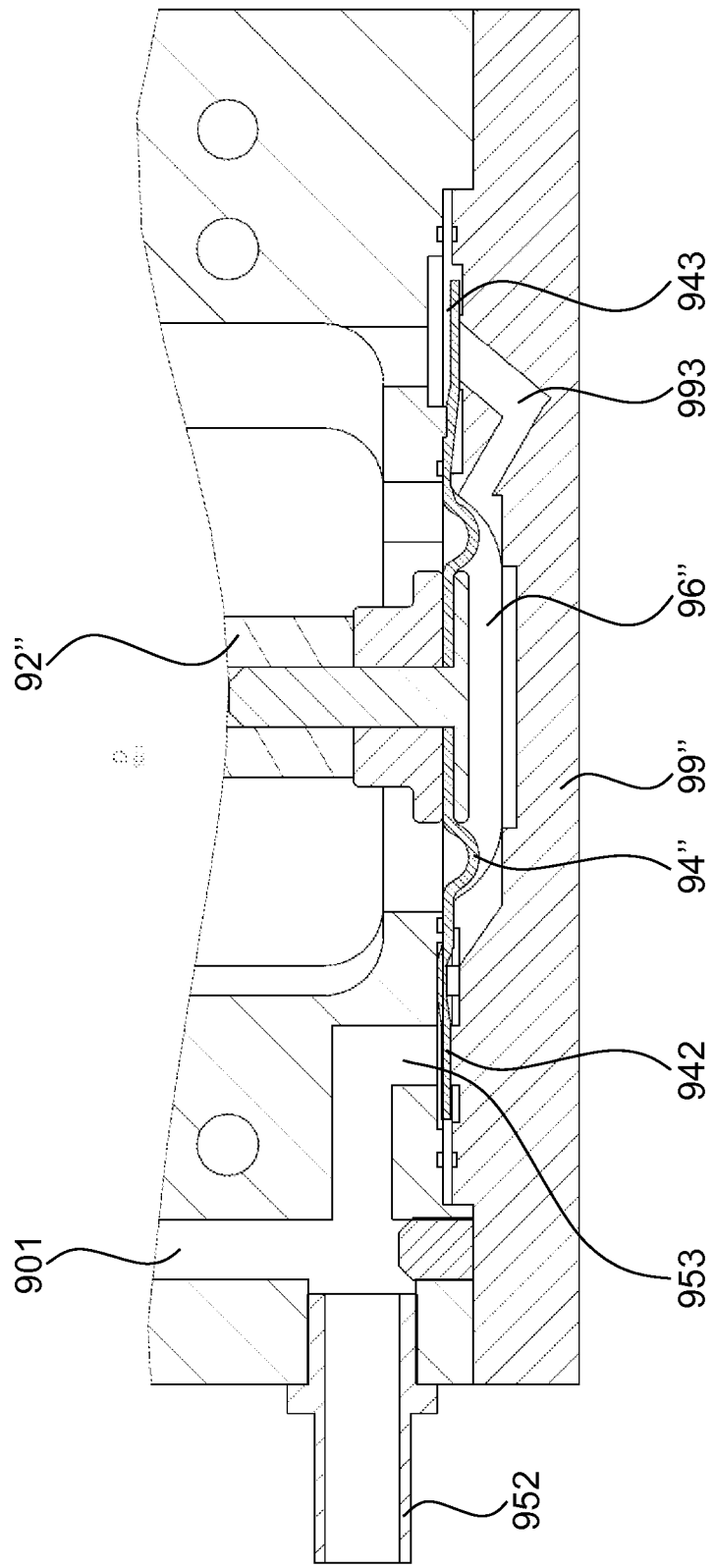
FIG. 14 shows an enlarged detail D according to FIG. 13 with a closed exhaust flap and open vacuum flap.

FIG. 14 shows this situation in the region of the vacuum diaphragm 94" on an enlarged scale. Because of to the raised vacuum diaphragm 94", the cover-side region of the vacuum chamber 96' has expanded and has a negative pressure. The outlet valve flap 943 is closed, by contrast the vacuum flap 942 is open, and therefore the negative pressure is applied via the vacuum channel 953 to the vacuum port 952. The ventilation channel 901 forms an additional dead volume, that also has to be evacuated. Since, however, the ventilation channel has a relatively small volume, the channel 901 has scarcely any negative effect on the efficiency of the pump unit.

Figure 15:
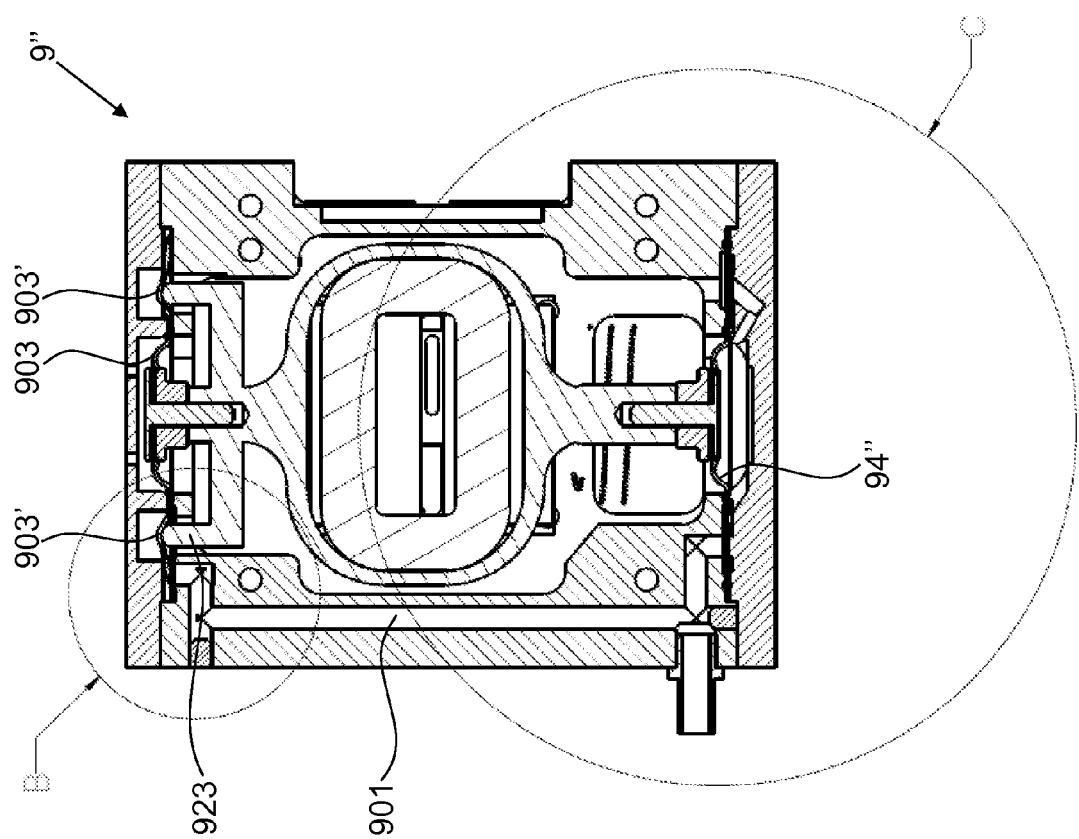
FIG. 15 shows a longitudinal section through the vacuum pump according to FIG. 7 during the ventilation.
Figure 16:
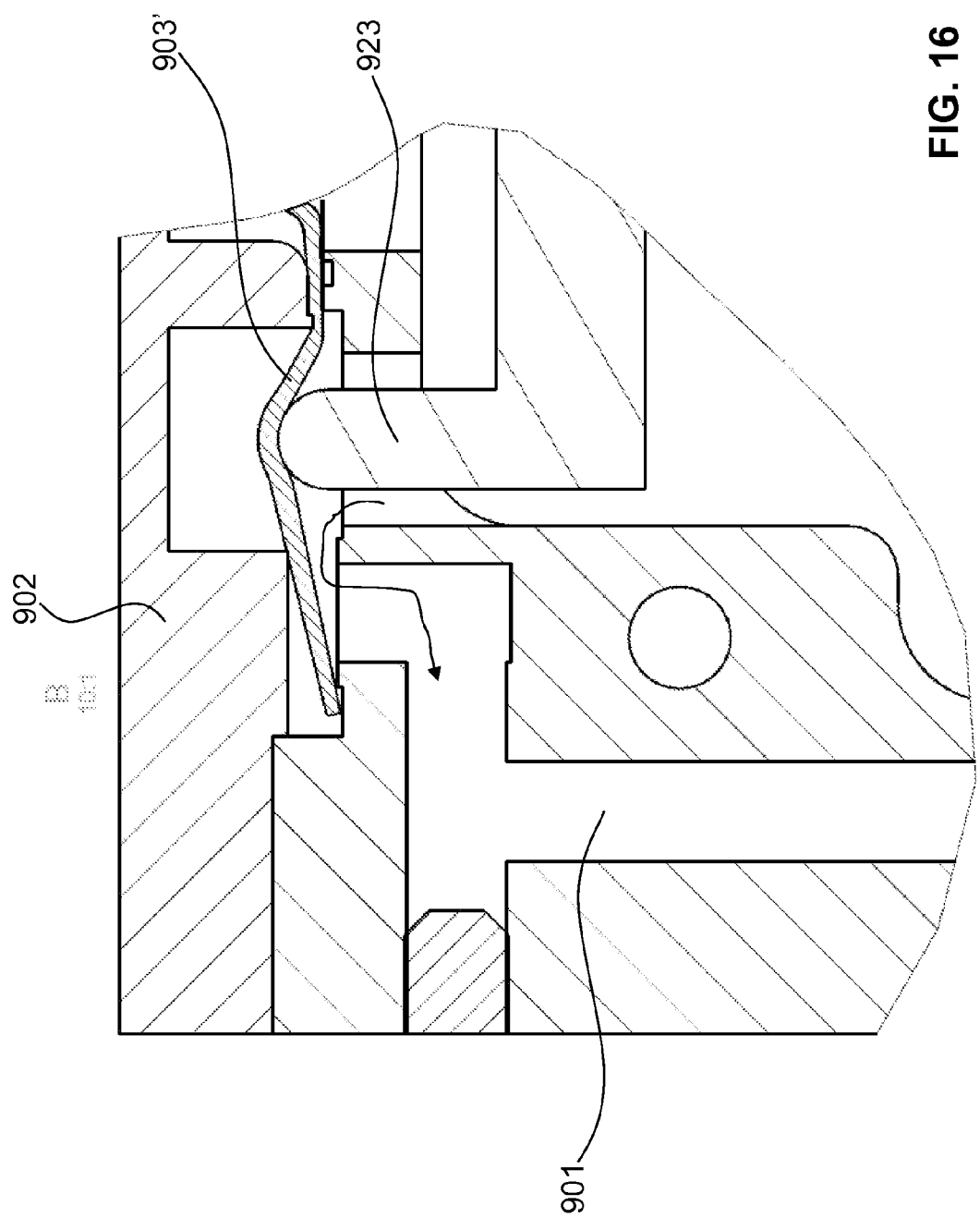
FIG. 16 shows an enlarged detail B according to FIG. 15 with an open ventilation flap.

FIG. 15 shows the coil former 92" in a third position in which it is raised even further. In this position, the actuators 923 raise the ventilation flaps 903' and thus open a connection to the ventilation channel 901. Air can pass from the housing 90" and from the outside through the channel 901 to the vacuum port 952 and can thus reduce the vacuum applied and raise the pressure to atmospheric pressure or to a desired base vacuum. This can readily be seen in FIG. 16. The arrow shows the path of the inflowing air.

As can be seen in FIG. 17, the vacuum diaphragm 94" is raised even further and is therefore ready for the next, vacuum-generating stroke. The vacuum flap 942 and also the outlet flap 943 are both raised and therefore open up the corresponding openings.

Therefore, in the pump unit according to the invention, the linear movement of the coil former 92" of the solenoid is converted into a parallel movement of the vacuum diaphragm. The same coil former 92" is also used for opening the ventilation valve, the movement of the coil former in the same direction as for the vacuum strokes being used for this purpose. Depending on the position of the coil former 92" relative to the permanent magnet 91" and therefore to the housing 90", a vacuum is generated or the ventilation is activated. To this end, only three different stroke positions of the coil former 99" are used. In this case, the third stroke, that activates the ventilation, is larger than each of the two other strokes, or it is at least larger than the stroke in the same direction for generating the vacuum. The three strokes can be generated by the electronic controller 15 in a controlled and targeted manner, in particular in terms of the magnitude thereof.

The third stroke, like the two other strokes, is generated by the electronic controller 15 of the unit 9". However, the third stroke does not have to take place in each cycle. As a result, pump sequences having different and varying curve courses and intervals can be generated.

The position scale enables the position of the coil former 92" relative to the housing 90" to be precisely identified and used for controlling the strokes. However, other ways of precisely identifying the position of the coil former 92" and the magnitude of the strokes are also possible.

It is furthermore advantageous that the two diaphragms, i.e. the vacuum diaphragm 94" and the ventilation diaphragm 903, serve as bearings for the movement of the coil former 92" and that therefore friction is avoided.

The inventive vacuum pump explained according to the above-described embodiments can be used, for example, in devices for expressing human breast milk. Examples of devices of this type are illustrated in FIGS. 3 to 6.

Figure 3:
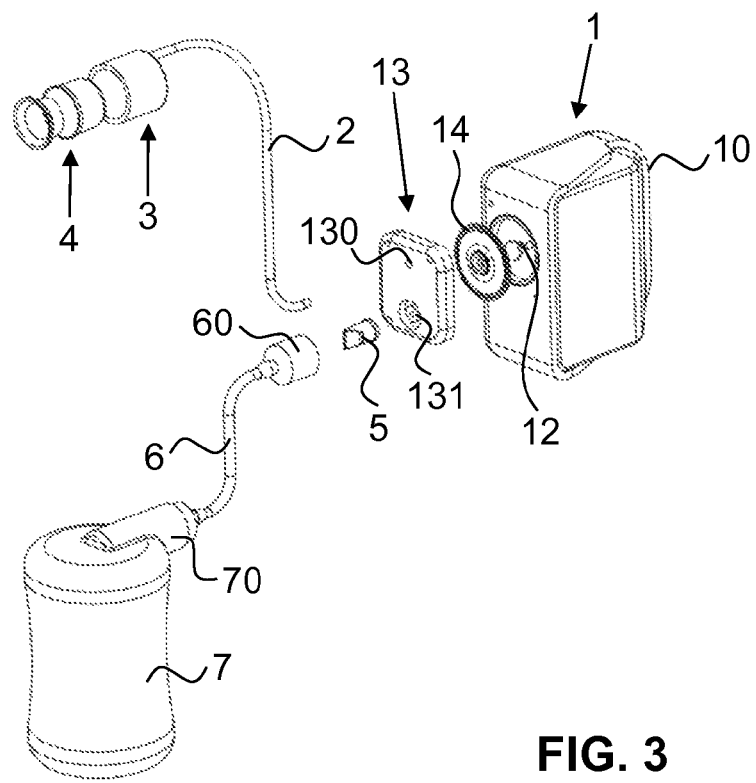
FIG. 3 shows an exploded view of a device for expressing breast milk with the vacuum pump according to the invention according to FIG. 1.

FIG. 3 illustrates a first embodiment of a device of this type. The device has a breastpump 1, a first line 2, a coupling part 3, a breast shield 4, a nonreturn valve 5, a second line 6 and a milk collecting container 7.

The breast shield 4 is connected to the breastpump 1 via the coupling part 3 and the first flexible line 2. The second flexible line 6 leads from the breastpump 1 to the milk collecting container 7, the connection being provided with the nonreturn valve 5. The two flexible lines 2, 6 are preferably tubes, in particular made of silicone.

Figure 4:
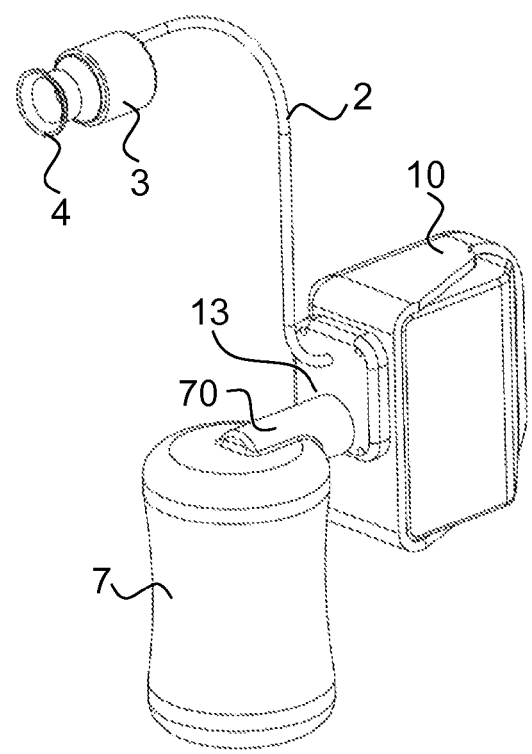
FIG. 4 shows a device for expressing breast milk in a second embodiment.

As illustrated in FIG. 4, the milk collecting container 7 may alternatively also be fastened directly to the breastpump 1. For this purpose, there is preferably a suitably shaped adaptor 70 on the milk collecting container 7, the adaptor being detachably connectable to a housing 10 of the breastpump.

The breastpump 1 has the abovementioned housing 10, in which the vacuum pump according to the invention, referred to below as a pump unit, is arranged together with a controller. The pump unit and the controller can be operated from the mains and/or battery operated.

There are control elements (not illustrated here) on the housing 10. The control elements may contain, inter alia, a switch on/off element, keys or buttons for selecting the pumping frequency and the applied vacuum and the period of duration of the expressing operation. There may also be a display.

A second chamber 8 (see FIG. 6), which acts as a pump chamber, is formed between a recess of the housing 10 and a cover 13 covering the recess. The cover 13 is preferably connected detachably to the housing 10. A diaphragm 14 which is held in its position by the cover 13 is arranged in the second chamber 8. The diaphragm 14 divides the pump chamber 8 into a unit-side part and a unit-remote part 80, 81, the diaphragm sealing the two parts with respect to each other.

Figure 5:
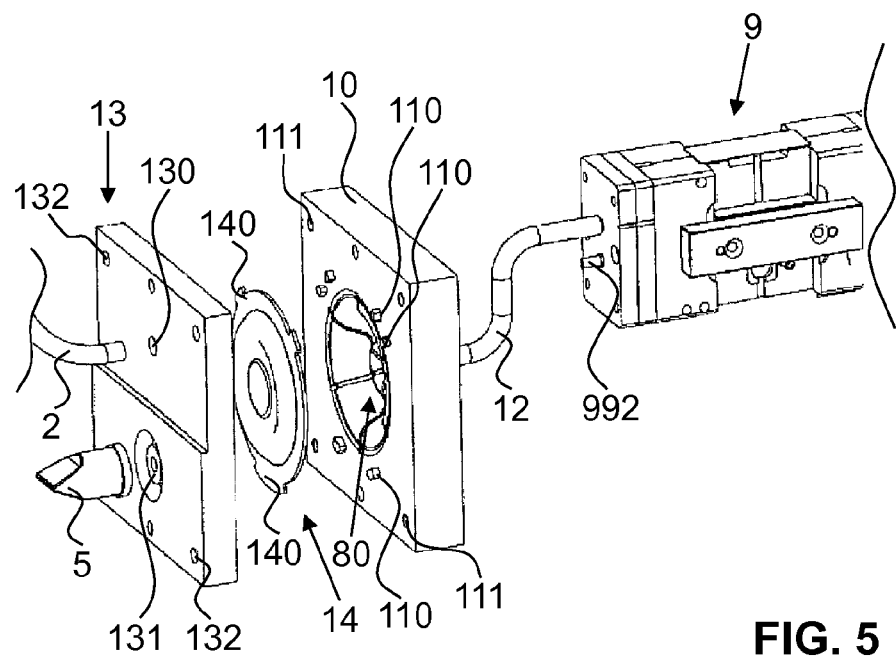
FIG. 5 shows an exploded view of a vacuum pump according to the invention in a first embodiment with part of the device according to FIG. 3.
Figure 6:
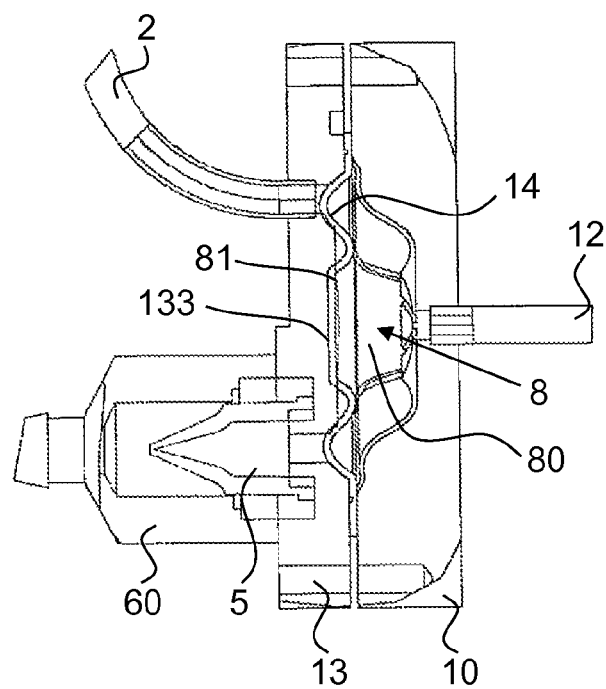
FIG. 6 shows a longitudinal section through part of the device according to FIG. 5.

As can be seen in FIG. 5, the diaphragm 14 illustrated here preferably has a substantially circular outline. There are preferably laterally protruding wings 140. There are three wings 140. The baseplate, which is preferably part of the housing 10, has lateral stops 110, between which the wings 140 are held. As a result, the diaphragm 14 can be held in an unambiguous position in the second chamber 8. This facilitates assembly.

The cover 13 has connecting ports for the first and second line 2, 6 and for the milk collecting container, respectively. The ports are provided with the reference numbers 130 and 131. The second port 131 is preferably provided with a non-return valve 5. The connection to the counterplate, which is part of the housing 10, preferably takes place via snap-in or screw connections, wherein the corresponding holes are provided with the reference numbers 132 and 111 in FIG. 5.

A vacuum, which has been generated in the pump unit, is transmitted via a line 12 to the second chamber 8. The line 12 is connected to the output 990. The changes in pressure are passed on via the vacuum line 12 to the second chamber 8 where the diaphragm 14 is moved analogously to the diaphragm 94.

The pump here can be operated with a temporally constant cycle or, as is known in the prior art, the suction curve may be adapted in the shape, frequency and intensity thereof to the suction behavior of the baby and/or to the requirements of the mother.

The second chamber 8 has inputs and outputs which are not all visible in the Figures. The cover 13 may be formed as a single piece or in a number of pieces. The cover 13 not only forms a tight closure, but also serves as a valve plate for the second pump chamber 8. Passages and valves (not illustrated in detail here) enabling the vacuum to build up in the unit-remote part, i.e. breast-side part 81, of the second pump chamber are therefore arranged in the cover 13.

In the cover 13 there is the first outlet opening 130 which connects the environment to the cover-side part 81 of the pump chamber 8. The outlet opening 130 serves as a first port for the first line 2. The second outlet opening 131, which connects the cover- and the breast-side part 81 of the second pump chamber 8 to the surroundings, respectively, is designed as a second port. The second port is provided with the nonreturn valve 5. Use is made here of a spout valve which is plugged onto a connector. However, other types of valve can also be used.

In use, the breast shield 4 is placed onto the mother's breast such that the breast shield at least surrounds the nipple. Preferably, at maximum the areola is additionally surrounded by the breast shield 4. The breastpump 1 is switched on and operated in the manner described above. The vacuum transmitted to the second pump chamber 8 evacuates the first line 2 such that there is a negative pressure in the breast shield 4. As a result, milk is expressed from the mother's breast and passes through the breast shield 4 and the coupling part 3 into the first line 2. The milk flows through the first port 130 into the cover-side part of the second pump chamber. The expressed milk leaves the second pump chamber 8 through the second port 131 and the nonreturn valve 5 and passes into the milk collecting container 7 via the second line 6 (see FIG. 3) or else, depending on the embodiment, directly (see FIG. 4). There is therefore no separate line for transporting the milk. The first line 2 serves at the same time as a suction line and as a milk transport line. After initial pneumatic pumping, the device therefore changes to hydraulic pumping. This is a further approximation to the natural suckling of babies.

The diaphragm 14 in the second pump chamber has two functions. First, it serves as a partition wall between the air in the pump-side part of the second pump chamber and the milk in the cover-side part of the second pump chamber. It therefore serves as a means of separating media and prevents milk from being able to pass into the vacuum line 12 and into the pump unit. However, it also prevents dirt from the pump unit from being able to pass into the first and second lines 2, 6. Secondly, the cyclic movement of the diaphragm within the second pump chamber results in the diaphragm conveying and transporting the milk. Thus, during the expressing operation, the milk collecting container 7, breast shield 4 and breastpump 1 can be arranged in positions which are independent of one another. For example, the milk collecting container 7 can be located above the breastpump 1 and/or the breast shield 4. The breastpump 1 may also be above the milk collecting container 7 and/or the breast shield 4. This enables the mother to express milk even while lying down or, if she is seated, to place the milk collecting container 7 and the breastpump 1 onto a shelf or another raised platform out of the reach of small children.

The nonreturn valve 5 preferably first opens at a sufficient pressure, i.e. when the second pump chamber 8 is sufficiently filled with milk. In this way, the dead volume which must be evacuated can be kept to a minimum.

In addition, the dead volume can be reduced by using a small breast shield 4 which only surrounds the nipple and as small a part of the remaining breast as possible, if any part at all. A suitable breast shield 4 is illustrated in the figures. Alternative forms of breast shields can also be used.

The elements of the above-described embodiments can be combined with one another individually or in groups in order to form further embodiments.

The vacuum pump according to the invention is relatively small and compact and operates quietly, and is suitable in particular for "hands free" breastpumps.

While the invention has been described herein with relation to certain embodiments and applications, those with skill in the art will recognize changes, modifications, alterations and the like which still come within the spirit of the inventive concept, and such are intended to be within the scope of the invention as expressed in the following claims.

The invention claimed is:

1. A diaphragm vacuum pump with an electrically operated drive unit and a vacuum diaphragm, the vacuum diaphragm separating a pump chamber into a drive-side part and a drive-remote part, wherein the vacuum diaphragm can be deflected by a movable part of the drive unit, wherein the drive unit is an electromagnetic drive unit, wherein the movement of the movable part is a linear movement and wherein the vacuum diaphragm is deflected in the direction of the linear movement which is generated electromagnetically in the drive unit, wherein the movable part is operatively connected to a ventilation valve for ventilating the diaphragm vacuum pump, wherein the ventilation valve has a ventilation diaphragm, wherein the vacuum diaphragm is fixedly connected to a first end of the movable part and the ventilation diaphragm is fixedly connected to a second end of the movable part, and wherein the vacuum diaphragm and the ventilation diaphragm form a mounting of the movable part within the drive unit, wherein the linear movement generated in the drive unit actuates the ventilation valve and wherein the movable part is movable by a controller in a first and a second stroke in order to generate a vacuum in the pump chamber, and is movable in a third stroke in order to actuate the ventilation valve, and wherein the third stroke is in the same direction of the second stroke and is larger than the second stroke.

2. The diaphragm vacuum pump as claimed in claim 1, wherein the first end of the movable part is opposite to the second end of the movable part.

3. The diaphragm vacuum pump as claimed in claim 1, wherein the drive unit has at least one permanent magnet and a coil former with a coil, wherein the coil is arranged on the coil former, wherein the coil former and the coil are held in a linearly displaceable manner in two directions along a longitudinal axis with respect to the magnet, and wherein the coil former forms the movable part and is fixedly connected to the vacuum diaphragm and deflects the vacuum diaphragm during the displacement of the coil former in both directions of the displacement of the coil former.

4. The diaphragm vacuum pump as claimed in claim 3, wherein the movable part comprises a piston formed by the coil former, the piston comprising a first and a second end, and wherein the vacuum diaphragm is arranged at the first end of the piston.

5. The diaphragm vacuum pump as claimed in claim 4, wherein the vacuum diaphragm has a diameter that is larger than the piston.

6. The diaphragm vacuum pump as claimed in claim 5, wherein the vacuum diaphragm is fastened centrally on the first end of the piston.

7. The diaphragm vacuum pump as claimed in claim 4, wherein the second end of the piston is held in a linearly displaceable manner.

8. The diaphragm vacuum pump as claimed in claim 4, wherein the ventilation diaphragm is fastened to the second end of the piston.

9. The diaphragm vacuum pump as claimed in claim 4, wherein the coil is a flat coil and wherein there is at least one permanent magnet, which is held in a fixed position in a housing of the diaphragm vacuum pump.

10. The diaphragm vacuum pump as claimed in claim 4, wherein the second end of the piston is mounted displaceably between an iron core and a magnet.

\* \* \* \* \*